US006951652B2

(12) United States Patent
Porro

(10) Patent No.: US 6,951,652 B2
(45) Date of Patent: Oct. 4, 2005

(54) VACCINE FOR PREVENTION OF GRAM-NEGATIVE BACTERIAL INFECTIONS AND ENDOTOXIN RELATED DISEASES

(75) Inventor: Massimo Porro, Siena (IT)

(73) Assignee: BioSynth S.r.l., Rapolano Terme (IT)

( * ) Notice: Subject to any disclaimer, the term of this patent is extended or adjusted under 35 U.S.C. 154(b) by 554 days.

(21) Appl. No.: 09/124,280

(22) Filed: Jul. 29, 1998

(65) Prior Publication Data

US 2002/0034520 A1 Mar. 21, 2002

(51) Int. Cl.$^7$ ............... A61K 39/02; A61K 39/108; A61K 39/112; A61K 38/00; A61K 38/12

(52) U.S. Cl. ............... 424/234.1; 424/185.1; 424/193.1; 424/236.1; 424/241.1; 424/250.1; 424/251.1; 424/258.1; 424/184.1; 424/260.1; 514/9; 514/11; 514/12; 514/14; 514/15; 514/16; 514/17; 530/300; 530/317; 530/324; 530/327; 530/328; 530/329; 530/350

(58) Field of Search ............... 424/234.1, 185.1, 424/184.1, 193.1, 236.1, 241.1, 250.1, 251.1, 258.1, 260.1; 514/9, 11, 12, 14–17; 530/300, 317, 324, 327, 328, 329, 350, 319

(56) References Cited

U.S. PATENT DOCUMENTS

| | | | | |
|---|---|---|---|---|
| 5,358,933 A | * | 10/1994 | Porro | 514/15 |
| 5,371,186 A | * | 12/1994 | Porro | 530/328 |
| 5,589,459 A | * | 12/1996 | Porro | 514/15 |
| 5,652,211 A | | 7/1997 | Porro | 514/11 |
| 5,688,767 A | * | 11/1997 | Hancock | 514/12 |
| 5,786,324 A | * | 7/1998 | Gray et al. | 514/9 |
| 5,837,250 A | * | 11/1998 | Kandil et al. | 424/185.1 |
| 6,290,971 B1 | * | 9/2001 | Kandil et al. | 424/237.1 |
| 6,579,696 B1 | * | 6/2003 | Shekhani et al. | 435/68.1 |
| 2002/0034520 A1 | * | 3/2002 | Porro | 424/234.1 |
| 2003/0040472 A1 | * | 2/2003 | Larsen et al. | 514/12 |
| 2003/0176325 A1 | * | 9/2003 | Nielsen et al. | 514/8 |
| 2004/0082505 A1 | * | 4/2004 | Ofek et al. | 514/9 |
| 2005/0020526 A1 | * | 1/2005 | Chen et al. | 514/44 |

FOREIGN PATENT DOCUMENTS

WO   9503327   *   2/1995

OTHER PUBLICATIONS

Rustici et al, Science, 1993, 259:361–365.*
Velucchi et al, J. endotoxin Research, 1997, 4/4:261–272.*
Iwagaki et al, Infection and Immunity, Mar, 2000, 68/3:1655–1663.*
Vaara et al, Antimicrobial Agents and Chemotherapy, Aug., 1996, 40/8:1801–1805.*
Velucchi et al, Vaccines 94 pp 141–146, 1994.*
Dr. Roger C. Bone. JAMA 276(7):565–566, 1996.*
Cross et al. Infection and Immunity 61(7):2741–2747, 1993.*
Velucchi et al. Journal of Endotoxin Research 4(4):261–272, 1997.*
Immunization Practices Advisory Committee. Clinical Pharmacy 8:839–850, 1989.*
Journal of Endotoxin Research (1997) 4(4), 261–272, "A Model of Neisseria Meningitidis Vaccine Based on LPS Micelles Detoxified by Synthetic Anti–Endotoxin Peptides", M. Velucchi et al.

* cited by examiner

Primary Examiner—Nita Minnifield
(74) Attorney, Agent, or Firm—Hedman & Costigan, P.C.

(57) ABSTRACT

A vaccine is disclosed which is useful for protecting a host from Gram negative infections and the effects of endotoxin, therefore preventing sepsis and septic shock. The vaccine is prepared by combining LPS free or in conjugate form with a stoichiometric excess of a peptide of the formula:

(a) $(A)_n$ wherein A is Lysine or Arginine and n is an integer with a minimum value of 7;

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

61 Claims, 10 Drawing Sheets

A

B

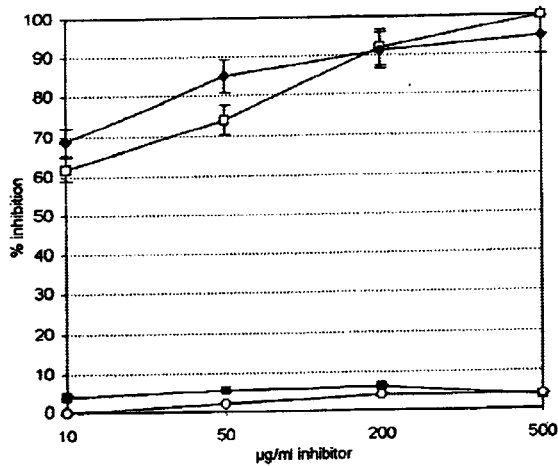

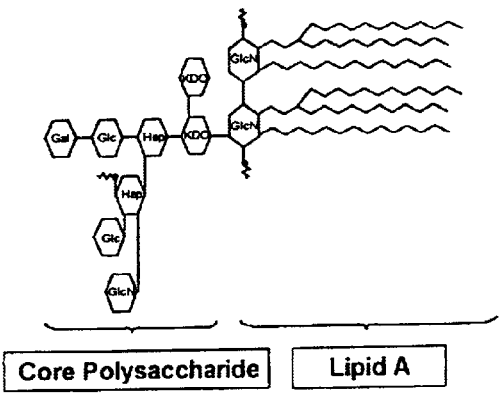

Schematic representation of the immunochemical specificity of mouse IgG polyclonal antibodies induced by endotoxoid A1. Analysis was performed by inhibition ELISA, at the serum dil. 1:800 (v/v) using homologous and heterologous LPS . ◆ N. meningitidis group A strain A1 LPS ; □ N. meningitidis group B strain BB431 LPS ; ■ S. minnesota LPS Re chemotype ; ○ E. coli O55:B5 LPS.

◯ : Monosaccharide ; • Phosphate ; ⁀ : Ethanolamin ;〜〜〜 : Long Chain (Hydroxy) Fatty Acid.

Fig 5a

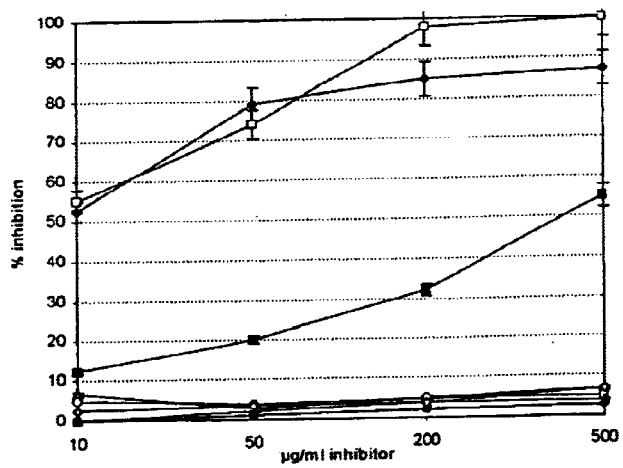

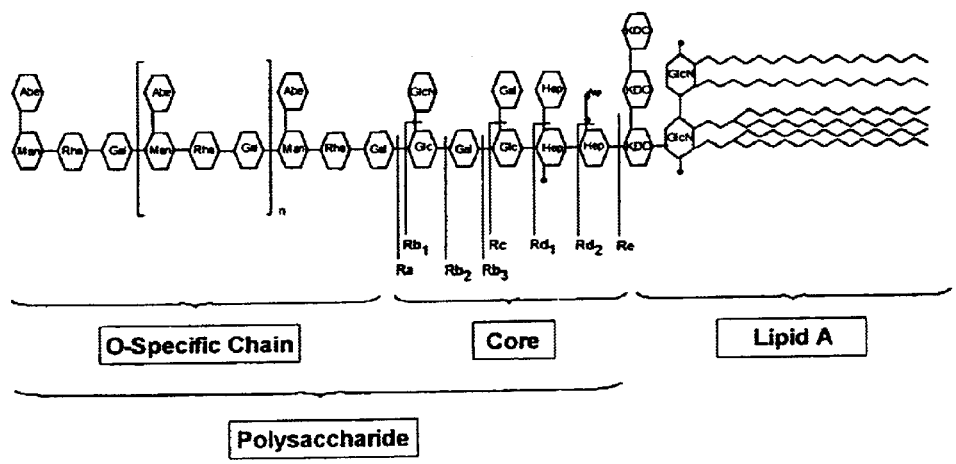

Schematic representation of the Immunochemical specificity of mouse IgG polyclonal antibodies induced by the endotoxoid Ty. Analysis was performed by inhibition ELISA, at the serum dil. 1:1,000 (v/v) using different LPS chemotypes from S. typhimurium. ☐ S. enterica LPS ; ◆ S. typhosa LPS ; ■ S. typhimurium LPS Ra chemotype ; △ S. typhimurium LPS Rb1 chemotype ; ○ S. typhimurium LPS Rc chemotype ; ▲ S. typhimurium LPS Rd2 chemotype ; ● S. typhimurium LPS Re chemotype ; ◇ SAEP2.

◯ : Monosaccharide ; • Phosphate ; ⌒ ; Ethanolamin ; ⋀⋁⋀ : Long Chain (Hydroxy) Fatty Acid.

Fig 5b

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 10 amino acids
      (B) TYPE: amino acid
      (C) TOPOLOGY: circular (ii) SEQUENCE DESCRIPTION: SEQ ID NO:1:

Lys Lys Lys Lys Lys Lys Lys Lys Lys Lys
1                 5                       10

(2) INFORMATION FOR SEQ ID NO:2:

(i) SEQUENCE CHARACTERISTICS:
      (A) LENGTH: 30 amino acids
      (B) TYPE: amino acid
      (C) TOPOLOGY: circular (ii) SEQUENCE DESCRIPTION: SEQ ID NO:2:

Lys Lys Lys Lys Lys Lys Lys Lys Lys Lys

```
                   1               5                  10
Lys Lys Lys Lys Lys Lys Lys Lys Lys Lys
                  15                                  20
Lys Lys Lys Lys Lys Lys Lys Lys Lys Lys
                  25                                  30
```

(2) INFORMATION FOR SEQ ID NO:3:

(i) SEQUENCE CHARACTERISTICS:
        (A) LENGTH: 434 amino acids
        (B) TYPE: amino acid
        (C) TOPOLOGY: circular (ii) SEQUENCE DESCRIPTION: SEQ ID NO:3:

```
Lys Lys Lys Lys Lys Lys Lys Lys Lys Lys
  1               5                  10
Lys Lys Lys Lys Lys Lys Lys Lys Lys Lys
                 15                  20
Lys Lys Lys Lys Lys Lys Lys Lys Lys Lys
                 25                  30
Lys Lys Lys Lys Lys Lys Lys Lys Lys Lys
                 35                  40
Lys Lys Lys Lys Lys Lys Lys Lys Lys Lys
                 45                  50
Lys Lys Lys Lys Lys Lys Lys Lys Lys Lys
                 55                  60
Lys Lys Lys Lys Lys Lys Lys Lys Lys Lys
                 65                  70
Lys Lys Lys Lys Lys Lys Lys Lys Lys Lys
                 75                  80
Lys Lys Lys Lys Lys Lys Lys Lys Lys Lys
                 85                  90
Lys Lys Lys Lys Lys Lys Lys Lys Lys Lys
                 95                 100
Lys Lys Lys Lys Lys Lys Lys Lys Lys Lys
                105                 110
Lys Lys Lys Lys Lys Lys Lys Lys Lys Lys
                115                 120
Lys Lys Lys Lys Lys Lys Lys Lys Lys Lys
                125                 130
Lys Lys Lys Lys Lys Lys Lys Lys Lys Lys
                135                 140
Lys Lys Lys Lys Lys Lys Lys Lys Lys Lys
                145                 150
Lys Lys Lys Lys Lys Lys Lys Lys Lys Lys
                155                 160
Lys Lys Lys Lys Lys Lys Lys Lys Lys Lys
                165                 170
Lys Lys Lys Lys Lys Lys Lys Lys Lys Lys
                175                 180
Lys Lys Lys Lys Lys Lys Lys Lys Lys Lys
                185                 190
Lys Lys Lys Lys Lys Lys Lys Lys Lys Lys
                195                 200
Lys Lys Lys Lys Lys Lys Lys Lys Lys Lys
```

```
                    205                 210
Lys Lys Lys Lys Lys Lys Lys Lys Lys Lys
                    215                 220
Lys Lys Lys Lys Lys Lys Lys Lys Lys Lys
                    225                 230
Lys Lys Lys Lys Lys Lys Lys Lys Lys Lys
                    235                 240
Lys Lys Lys Lys Lys Lys Lys Lys Lys Lys
                    245                 250
Lys Lys Lys Lys Lys Lys Lys Lys Lys Lys
                    255                 260
Lys Lys Lys Lys Lys Lys Lys Lys Lys Lys
                    265                 270
Lys Lys Lys Lys Lys Lys Lys Lys Lys Lys
                    275                 280
Lys Lys Lys Lys Lys Lys Lys Lys Lys Lys
                    285                 290
Lys Lys Lys Lys Lys Lys Lys Lys Lys Lys
                    295                 300
Lys Lys Lys Lys Lys Lys Lys Lys Lys Lys
                    305                 310
Lys Lys Lys Lys Lys Lys Lys Lys Lys Lys
                    315                 320
Lys Lys Lys Lys Lys Lys Lys Lys Lys Lys
                    325                 330
Lys Lys Lys Lys Lys Lys Lys Lys Lys Lys
                    335                 340
Lys Lys Lys Lys Lys Lys Lys Lys Lys Lys
                    345                 350
Lys Lys Lys Lys Lys Lys Lys Lys Lys Lys
                    355                 360
Lys Lys Lys Lys Lys Lys Lys Lys Lys Lys
                    365                 370
Lys Lys Lys Lys Lys Lys Lys Lys Lys Lys
                    375                 380
Lys Lys Lys Lys Lys Lys Lys Lys Lys Lys
                    385                 390
Lys Lys Lys Lys Lys Lys Lys Lys Lys Lys
                    395                 400
Lys Lys Lys Lys Lys Lys Lys Lys Lys Lys
                    405                 410
Lys Lys Lys Lys Lys Lys Lys Lys Lys Lys
                    415                 420
Lys Lys Lys Lys Lys Lys Lys Lys Lys Lys
                    425                 430
Lys Lys Lys Lys (2) INFORMATION FOR SEQ ID NO:4:

(i) SEQUENCE CHARACTERISTICS:
        (A) LENGTH:   10 amino acids
        (B) TYPE:     amino acid
        (C) TOPOLOGY: circular (ii) SEQUENCE DESCRIPTION: SEQ ID NO:4:
```

```
Lys Asp Lys Asp Lys Asp Lys Asp Lys Asp
1               5                   10
```

(2) INFORMATION FOR SEQ ID NO:5:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:5:

```
Lys Phe Lys Phe Lys Phe Lys Phe Lys Phe
1               5                   10
```

(2) INFORMATION FOR SEQ ID NO:6:

(i) SEQUENCE CHARACTERISTICS:
        (A) LENGTH: 7 amino acids
        (B) TYPE: amino acid
        (C) TOPOLOGY: circular (ii) SEQUENCE DESCRIPTION: SEQ ID NO:6:

```
Lys Phe Leu Lys Lys Thr Leu
1               5
```

(2) INFORMATION FOR SEQ ID NO:7:

(i) SEQUENCE CHARACTERISTICS:
        (A) LENGTH: 7 amino acids
        (B) TYPE: amino acid
        (C) TOPOLOGY: circular (ii) SEQUENCE DESCRIPTION: SEQ ID NO:7:

```
Lys Phe Leu Lys Phe Leu Lys
1               5
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: circular (ii) SEQUENCE DESCRIPTION: SEQ ID NO:8:

```
Lys Phe Leu Lys Phe Leu Lys Phe Leu Lys
1               5                   10
```

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: circular (ii) SEQUENCE DESCRIPTION: SEQ ID NO:9:

```
Arg Tyr Val Arg Tyr Val Arg Tyr Val
1               5
```

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: circular (ii) SEQUENCE DESCRIPTION: SEQ ID NO:10:

```
Lys Phe Phe Lys Phe Phe Lys Phe Phe Lys
1               5                   10
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: circular (ii) SEQUENCE DESCRIPTION: SEQ ID NO:11:

```
Lys Leu Leu Lys Leu Leu Lys Leu Leu
1               5
```

(2) INFORMATION FOR SEQ ID NO:12:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:12:

```
Lys Lys Lys Lys Lys Lys Phe Lys Phe Lys
1               5                   10
```

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: circular (ii) SEQUENCE DESCRIPTION: SEQ ID NO:13:

```
Cys Lys Cys Lys Cys Lys Cys Lys Cys Lys Cys
1               5                   10
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: circular (ii) SEQUENCE DESCRIPTION: SEQ ID NO:14:

```
Cys Lys Phe Lys Lys Cys
1               5
```

(2) INFORMATION FOR SEQ ID NO:15:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:15:

```
Lys Phe Lys Cys Lys Phe Lys Phe Lys Cys
1               5                   10
```

(2) INFORMATION FOR SEQ ID NO:16:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:16:

```
Lys Leu Lys Cys Lys Leu Lys Leu Lys Cys
```

(2) INFORMATION FOR SEQ ID NO:17:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:17:

```
Arg Thr Arg Cys Arg Phe Lys Arg Arg Cys
1               5                   10
```

(2) INFORMATION FOR SEQ ID NO:18:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:18:

```
Lys Cys Lys Phe Lys Lys Phe Lys Cys Lys
1               5                   10
```

(2) INFORMATION FOR SEQ ID NO:19:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:19:

```
Cys Lys Lys Lys Lys Phe Phe Phe Phe Cys
1               5                   10
```

(2) INFORMATION FOR SEQ ID NO:20:

(i) SEQUENCE CHARACTERISTICS:
        (A) LENGTH: 12 amino acids
        (B) TYPE: amino acid
        (D) TOPOLOGY: circular (ii) SEQUENCE DESCRIPTION: SEQ ID NO:20:

```
Cys Lys Phe Leu Lys Phe Leu Lys Phe Leu Lys Cys
1               5                   10
```

(2) INFORMATION FOR SEQ ID NO:21:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:21:

```
Val Lys Ala Leu Arg Val Arg Arg Leu
1               5
```

(2) INFORMATION FOR SEQ ID NO:22:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:22:

```
Lys Ser Leu Ser Leu Lys Arg Leu Thr Tyr Arg
1               5                   10
```

(2) INFORMATION FOR SEQ ID NO:23:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:23:

```
Lys Val Arg Lys Ser Phe Phe Lys Val
1               5
```

(2) INFORMATION FOR SEQ ID NO:24:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:24:

```
Phe Leu Lys Pro Gly Lys Val Lys Val
1               5
```

(2) INFORMATION FOR SEQ ID NO:25:

(i) SEQUENCE CHARACTERISTICS:
        (A) LENGTH: 8 amino acids
        (B) TYPE: amino acid
        (C) TOPOLOGY: circular (ii) SEQUENCE DESCRIPTION: SEQ ID NO:25:

```
Lys Glu Leu Lys Arg Ile Lys Ile
1               5
```

(2) INFORMATION FOR SEQ ID NO:26:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:26:

```
Lys Trp Lys Ala Gln Lys Arg Phe Leu
1               5
```

(2) INFORMATION FOR SEQ ID NO:27:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:27:

```
Lys Trp Lys Ala Gln Lys Arg Phe Leu Lys
1               5                   10
```

(2) INFORMATION FOR SEQ ID NO:28:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:28:

```
Lys Arg Leu Lys Trp Lys Tyr Lys Gly Lys Phe
1               5                   10
```

(2) INFORMATION FOR SEQ ID NO:29:

(i) SEQUENCE CHARACTERISTICS:
        (A) LENGTH: 13 amino acids
        (B) TYPE: amino acid
        (C) TOPOLOGY: circular (ii) SEQUENCE DESCRIPTION: SEQ ID NO:29:

Cys Gln Ser Trp Lys Ser Ser Glu Ile Arg Cys Gly Lys
1               5                   10

(2) INFORMATION FOR SEQ ID NO:30:

(i) SEQUENCE CHARACTERISTICS:
        (A) LENGTH: 7 amino acids
        (B) TYPE: amino acid
        (C) TOPOLOGY: circular (ii) SEQUENCE DESCRIPTION: SEQ ID NO:30:

Cys Lys Phe Leu Lys Lys Cys
1               5

(2) INFORMATION FOR SEQ ID NO:31:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:31:

Lys Thr Lys Cys Lys Phe Leu Lys Lys Cys
1               5                   10

(2) INFORMATION FOR SEQ ID NO:32:

(i) SEQUENCE CHARACTERISTICS:
        (A) LENGTH: 6 amino acids
        (B) TYPE: amino acid
        (C) TOPOLOGY: circular (ii) SEQUENCE DESCRIPTION: SEQ ID NO:32:

Lys Phe Leu Lys Lys Thr
1               5

(2) INFORMATION FOR SEQ ID NO:33:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:33:

Cys Lys Lys Leu Phe Lys Cys Lys Thr Lys
1               5                   10

(2) INFORMATION FOR SEQ ID NO:34:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:34:

Cys Lys Lys Leu Phe Lys Cys Lys Thr
1               5

(2) INFORMATION FOR SEQ ID NO:35:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:35:

Ile Lys Thr Lys Cys Lys Phe Leu Lys Lys Cys
1               5                   10

(2) INFORMATION FOR SEQ ID NO:36:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:36:

Ile Lys Thr Lys Lys Phe Leu Lys Lys Thr
1               5                   10

(2) INFORMATION FOR SEQ ID NO:37:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:37:

Ile Lys Phe Leu Lys Phe Leu Lys Phe Leu Lys
1               5                   10

(2) INFORMATION FOR SEQ ID NO:38:

(i) SEQUENCE CHARACTERISTICS:
        (A) LENGTH: 7 amino acids
        (B) TYPE: amino acid
        (C) TOPOLOGY: circular (ii) SEQUENCE DESCRIPTION: SEQ ID NO:38:

Lys Phe Leu Lys Phe Leu Lys
1               5

(2) INFORMATION FOR SEQ ID NO:39:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:39:

Arg Tyr Val Arg Tyr Val Arg Tyr Val
1               5

(2) INFORMATION FOR SEQ ID NO:40:

(i) SEQUENCE CHARACTERISTICS:
        (A) LENGTH: 9 amino acids
        (B) TYPE: amino acid
        (C) TOPOLOGY: circular (ii) SEQUENCE DESCRIPTION: SEQ ID NO:40:

Lys Phe Phe Lys Phe Phe Lys Phe Phe
1               5

(2) INFORMATION FOR SEQ ID NO:41:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:41:

Ile Lys Phe Leu Lys Phe Leu Lys Phe Leu
1               5                   10

(2) INFORMATION FOR SEQ ID NO:42:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:42:

Lys Lys Lys Lys Lys Lys Phe Leu Phe Leu
1               5                   10

(2) INFORMATION FOR SEQ ID NO:43:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:43:

Cys Lys Phe Lys Phe Lys Phe Lys Phe Cys
1               5                   10

(2) INFORMATION FOR SEQ ID NO:44:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:44:

Lys Trp Lys Ala Gln Lys Arg Phe Leu Lys
1               5                   10

(2) INFORMATION FOR SEQ ID NO:45:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:45:

Lys Arg Leu Lys Trp Lys Tyr Lys Gly Lys Phe
1               5                   10

VACCINE FOR PREVENTION OF GRAM-NEGATIVE BACTERIAL INFECTIONS AND ENDOTOXIN RELATED DISEASES

The present invention is concerned with providing a vaccine for prevention of bacterial infections caused by gram-negative bacteria and for the prevention of the biological effects of homologous endotoxins.

BACKGROUND OF THE INVENTION

LPS is the major antigen of gram-negative bacteria. This material is a glycophospholipid consisting of an antigenic, variable size, carbohydrate chain covalently linked to lipid A, the conserved hydrophobic region structurally defined as N,O-acyl beta-1,6-D-glucosamine 1,4'-bisphosphate. Toxicity of LPS is expressed by lipid A through the interaction with B-cells and macrophages of the mammalian immune system, a process leading to the secretion of proinflammatory cytokines, mainly TNF, which may have fatal consequences for the host. Lipid A also activates human T-lymphocytes (Th-1) "in vitro" as well as murine CD4+ and CD8+ T-cell "in vivo", a property which allows the host's immune system to mount a specific, anamnestic IgG antibody response to the variable-size carbohydrate chain of LPS. On these bases, LPS has been recently recognized as a T-cell dependent antigen "in vivo".

In order to fully express toxicity, LPS must retain its supramolecular architecture, through the association of several units of glycophospholipid monomers forming the lipid A structure. This conformational rearrangement of the molecule is also fundamental for full expression of the immunogenic characteristic. Therefore, dissociation of these intrinsic properties of the molecule appear to be of crucial interest for proposing the design of LPS-based vaccines related to the prophylaxis of acute and chronic pathologies due to gram-negative bacterial infections like meningococcal meningitis, typhoid fever and *Helicobacter pylori*-induced gastritis.

Sepsis and septic shock are well defined clinical conditions that are caused by bacteria and by LPS which is the endotoxin elaborated by the bacteria responsible for the above mentioned pathologies. The present inventor has described treatment regimens for septic shock which are based on the use of a defined class of peptides that have been demonstrated to be capable of neutralizing LPS in vivo and protecting mammal from septic shock induced by LPS.

The treatment of a subject for septic shock requires that the subject who has symptoms of LPS toxicity be given the peptide when symptoms appear. The peptide is not an immunogenic compound for the production of antibodies to LPS and it use prophylactically will not prevent sepsis which is caused by the bacteria which release LPS. LPS has immunogenic properties but it is too toxic to be used to induce the production of antibodies in a host who is to be protected from the effects of a bacterial infection and from the effects of LPS which is released by certain bacterial infections.

Certain of the peptides are disclosed in U.S. Pat. No. 5,371,186, and information about the basis of the vaccine is disclosed in J. Endotoxin Res. (1997) 4(4)261–272, which is incorporated by reference.

SUMMARY OF THE INVENTION

The applicant has discovered that a vaccine may be prepared by making an endotoxoid that is made by combining LPS free or in conjugate form with a stoichiometric excess of a peptide of the formula:

(a) $(A)_n$ wherein A is Lysine or Arginine and n is an integer with a minimum value of 7;

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2. The peptides of the invention may be terminated independently with a hydrogen atom or any of the naturally occurring amino acids, a fatty acid residue or a carbohydrate residue.

The vaccine is particularly useful for the prevention of gram-negative infections and prevents the effects of endotoxins produced by said gram-negative infections.

Accordingly, it is a primary object of the invention to provide a method for preparing a vaccine for the prevention of sepsis and septic shock;

It is also an object of the invention to provide a novel vaccine for the prevention of sepsis and septic shock.

It is also an object of the invention to provide a novel vaccine based on an endotoxoid complex of LPS/peptide or conjugated LPS/peptide complex derived from homologous LPS.

It is also an object of this invention to provide novel compositions and methods for the treatment of microbial infections.

These and other objects of the invention will become apparent from the appended specification.

```
(SAEP2 is: Lys-Thr-Lys-Cys-Lys-Phe-Leu-Lys-Lys-Cys)
                     s - - - - - - - - - - - s
``` complex (ratio LPS A1/SAEP2=1:250(v/v)); inverted open triangle BSA-LPS A1; filled circle BSA-LPS A1/peptide SAEP2 complex (ratio LPS A1/SAEP2=1:250 (v/v)). The titers of IgG, represented by the OD value of each symbol were detected by ELISA in the sera pool of each animal group at a standard dilution of 1:200(v/v)

Figure 2A:
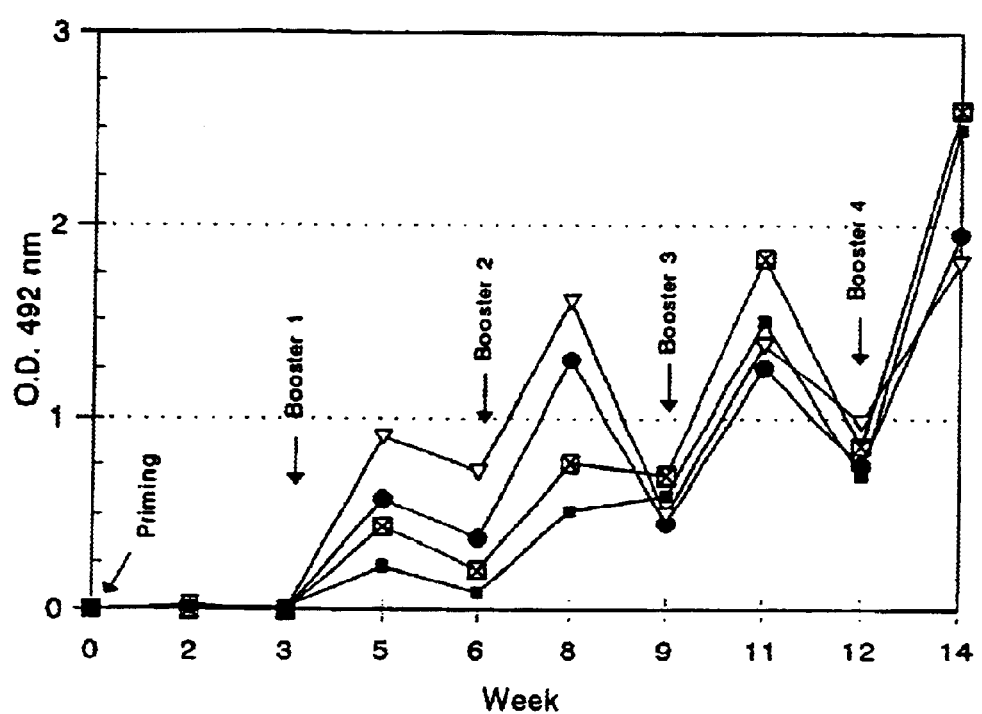
FIG. 2a comprises a graph which illustrates the kinetic of serum IgG production in SW mice induced by LPS A1, using IgG which is specific for LPS A1. The filled squares are LPS A1; open squares with the cross are LPS A1/SAEP2 peptide (SAEP is.
Figure 2B:
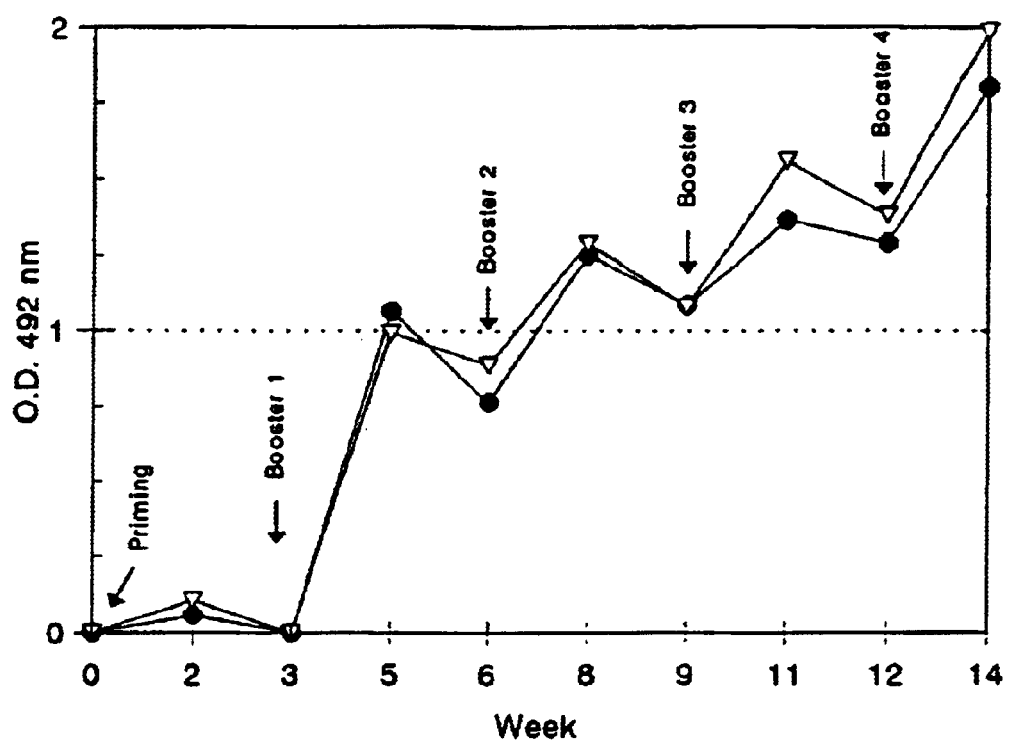

FIG. 2b comprises a graph which is similar to FIG. 2a except that the serum was specific for the carrier protein BSA.

Figure 3:
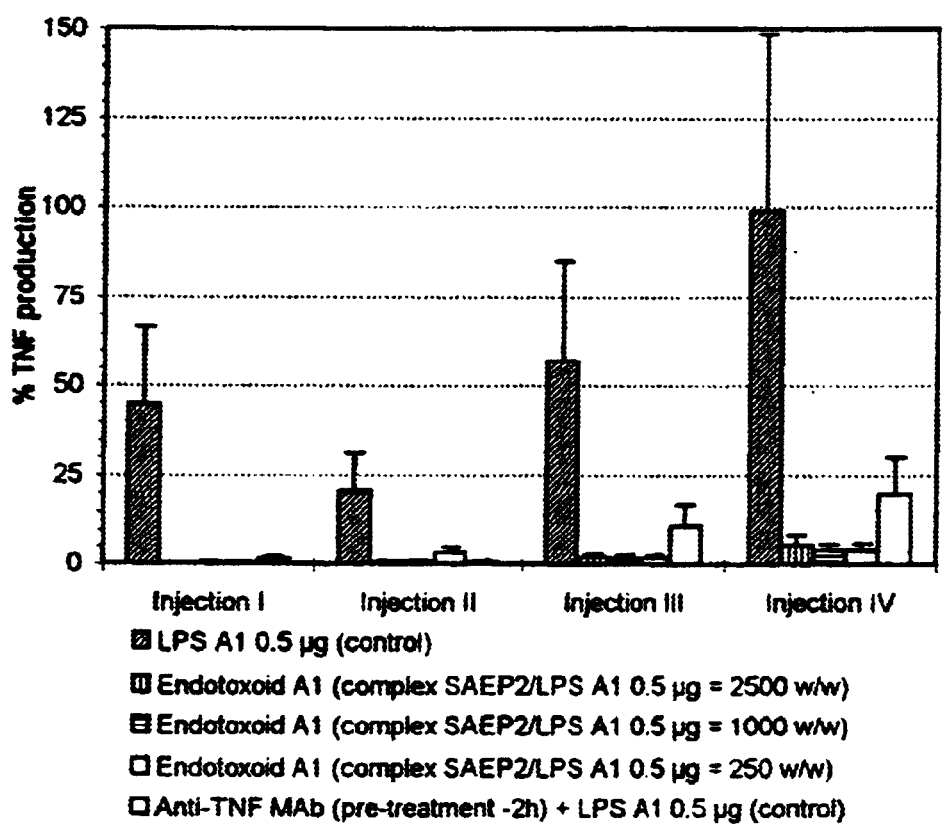

FIG. 3 is a graph which illustrates the lack of toxicity by quantitation of the TNF release in the serum of SW mice 90 min. after s.c. injections (3 weeks apart), of endotoxoid of *N. meningitidis* A1 prepared in different formulations.

Figure 4A:
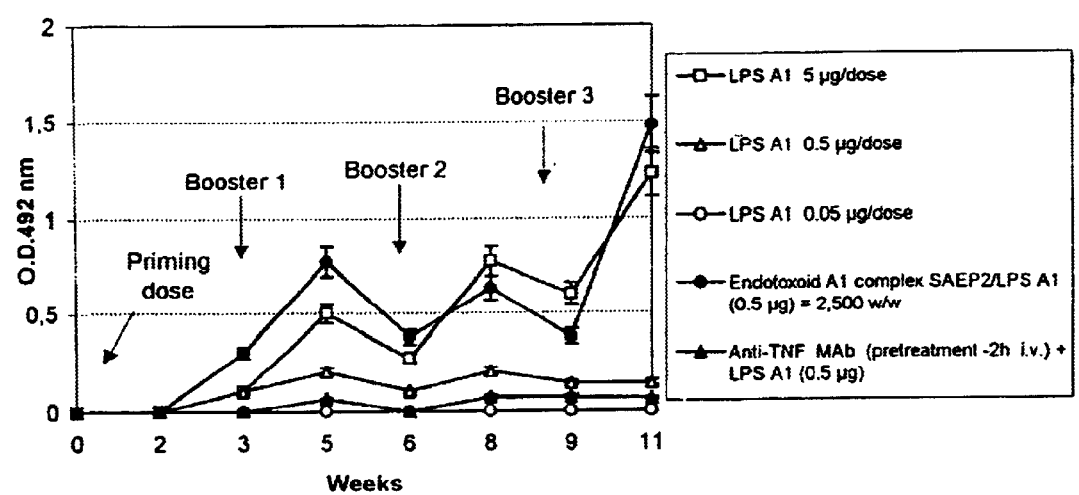

FIG. 4a shows the kinetic of serum IgG production in SW mice induced by four doses of endotoxoid of *N. meningitidis* A1 injected s.c. three weeks apart. All sera were diluted at 1:800(v/v).

Figure 4B:
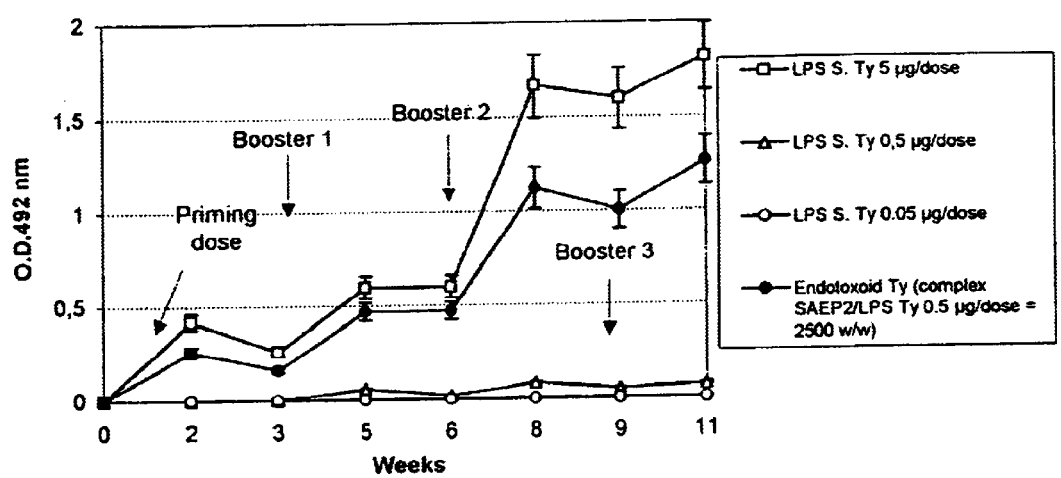

FIG. 4b shows the kinetic of serum IgG production in CD1 mice induced by four doses of endotoxoid of *Salmonella typhimurium* injected s.c. three weeks apart. All sera were diluted at 1:10,000(v/v).

FIG. 5a is a graph which shows the immunochemical specificity of mouse IgG antibody induced by the endotoxoid A1 prepared from *N. meningitidis* Strain A1.

FIG. 5b is a graph which shows the immunochemical specificity of mouse IgG antibody induced by the endotoxoid Ty prepared from *S.enterica* (*Serovar typhimurium*).

Figure 6A:
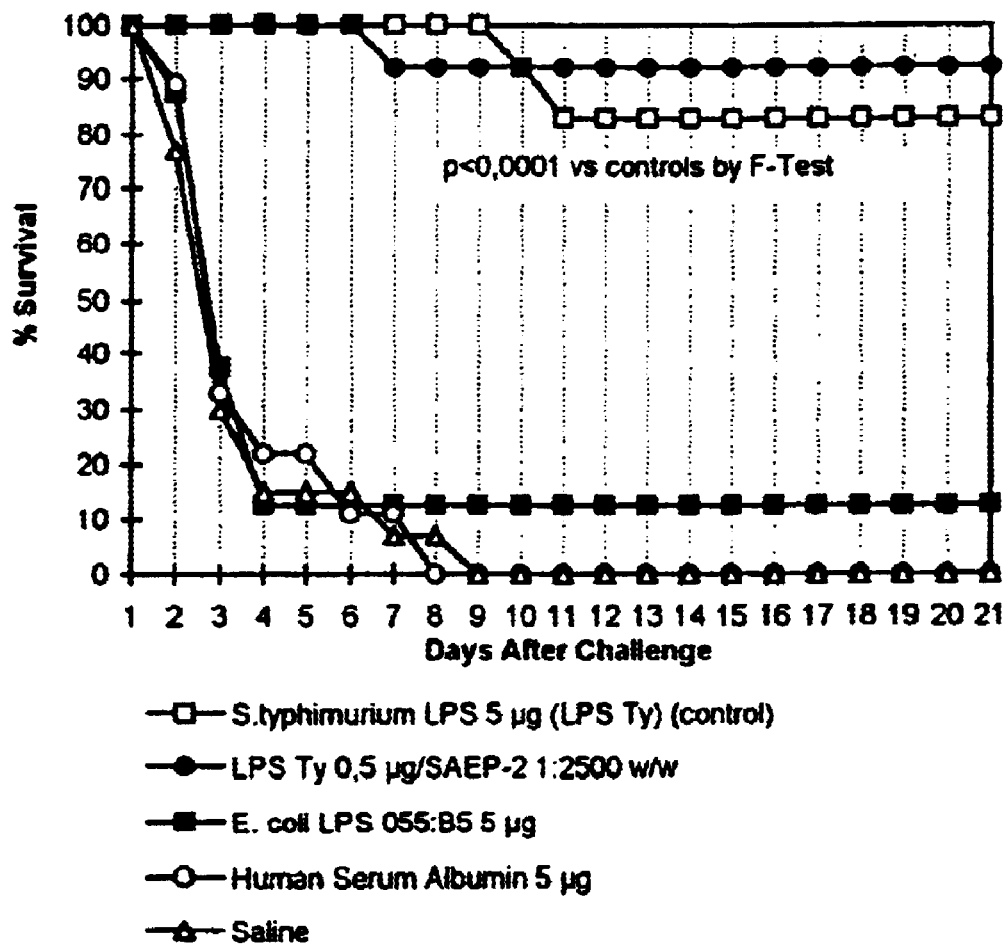

FIG. 6a is a graph which shows the protection against an i.p. challenge of *S. enterica* (*Serovar typhimurium*) in CD1 mice immunized either with endotoxoid Ty or homologous/heterologous antigens as controls where the $LD_{100}$ (dose of bacteria killing 100% of the animal population) is $4 \times 10^5$ cells.

Figure 6B:
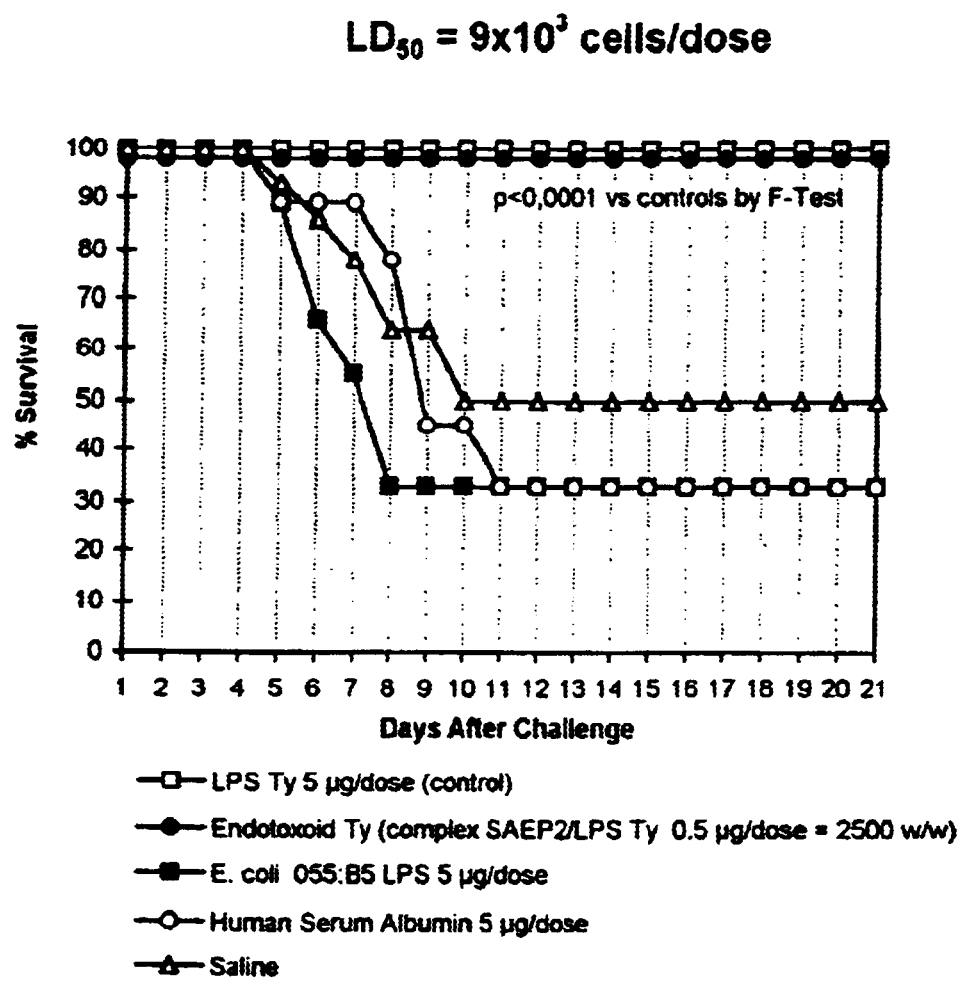

FIG. 6b is a graph which is the same as FIG. 5a except that it shows the protection against an i.p. challenge of *S. enterica* in CD1 mice immunized either with endotoxoid Ty or homologous/heterologous antigens as controls where the $LD_{50}$ is $9 \times 10^3$ cells.

DETAILED DESCRIPTION OF THE INVENTION

The toxic characteristics of LPS may be abrogated without elimination of the antigenic and immunogenic properties of LPS by binding the LPS (via the lipid A moiety) to a peptide as defined in the present application. Typical species of bacteria which produce LPS include *N. meningitidis* Group A,B,C. W135, Y; *E. coli* (especially strain 0157); *Salmonella typhi; Salmonella paratyphi*; (A and B) *Shigella flexneri*; non-typeable *Haemophilus influenzae; Haemophilus influenzae*, type b; *Helicobacter pylori; Chlamydia trachomatis; Chlamydia pneumoniae; Bordatella pertussis; Brucella; Legionella pneumophia; Vibrio cholera* (type 01 and non-01); *Moraxella catharralis; Pseudomonas aeruginosa*; and *Klebsiella pneumonia* (all species). In particular, the toxicity of structurally different LPS' has been completely abrogated by a lipid A-binding cyclic decapeptide, without affecting the structural integrity of the lipid A moiety and the supramolecular architecture of the antigen. It has been found that different LPS' exhibit an active lipid A moiety with a binding site which can be stoichiometrically saturated in vitro, with high affinity, with a peptide according to the present invention. However, it has been found that for in vivo detoxification of LPS with a peptide according to the present invention, it is necessary to use an excess of peptide with respect to the stoichiometric amount required "in vitro" to sufficiently detoxify LPS for preparing an immunogenic endotoxoid (complex) which will induce antibody formation without any unacceptable toxicity. It is believed that the stoichiometric excess is necessary to significantly stabilize the LPS-peptide complex from the likely antagonistic activity of natural LPS-receptor proteins present on specialized cells of the immune system which bear amino acid sequences similar to that of the peptides used in the present invention.

Generally, the immunogenic compound, or endotoxoid complex of the invention, is prepared by combining LPS, derived from a bacterial source, with from 2–10 to 2–5000, preferably from 10–5000 and especially preferably from 250–2500 times its weight, of a peptide as described herein based on a weight/weight ratio of LPS to the peptide. Higher molecular weight peptides may require a higher ratio of peptide to LPS. It is also possible to first conjugate the LPS with a protein such as bovine serum albumin, tetanus toxoid or diphtheria toxoid or non-toxic diphtheria mutant proteins (CRM197) or outer-membrane proteins (OMP) prior to combining the LPS with the peptide to form the endotoxoid complex. Generally a ratio of 2:1 of LPS to BSA may be employed in the conjugation procedure to yield a covalent conjugate of LPS:BSA=1 (w/w).

The peptides which may be complexed with the lipid A moiety of LPS include linear or cyclic peptides having units of the formula:

(a) $(A)_n$ wherein A is Lysine or Arginine and n is an integer with a minimum value of 7;

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2. The peptides of the invention may be terminated independently with a hydrogen atom or any of the naturally occurring amino acids, a fatty acid residue or a carbohydrate residue. In addition the retro-inverted peptides, the enantiomer amino acid sequences (all -D amino acids in the sequence), the diastereomer amino acid sequences (-D and -L amino acids in the sequence), and the peptide sequences in which the amino acids are inverted with respect to their original position in the sequence which are based on the peptides described herein may also be employed.

The preferred peptides for use in the invention will also have a ratio of aliphatic cationic amino acids to hydrophobic amino acids ($R_{c/h}$) of at least 0.5 and within the range of about 0.5 to 10.0 which is computed by using the solvent parameter values only for those amino acids which are present in the peptides which have a solvent parameter value equal to or greater than +1.5kcal/mol (lysine and arginine) and −1.5 kcal/mol (valine, isoleucine,leucine, tyrosine, phenylalanine and tryptophane) as measured according to Levitt, J. Mol. Biol. 104,59 (1976), which is incorporated by reference.

The peptide sequence for use in preparing a vaccine according to the invention will preferably comprise six to ten amino acid residues containing a minimum of three aliphatic cationic amino acids, with a ratio of aliphatic cationic amino acids to hydrophobic amino acids of equal to or greater than 0.5 ($R_{c/h}$ wherein c is the number of cationic amino acids in the peptide and h is the number of hydrophobic amino acids in the peptide). This ratio is believed to be the minimum although sequences of ten amino acids with a ratio ($R_{c/h}$) equal to or greater than 1.0 are optimal for expression of biological activity.

The peptide units which are represented by formula (a), (b) and (c) represent discrete peptides which will also potentiate antibiotics as well as peptides which will bind and neutralize endotoxin in the LAL test and which include as a part of their structure units of formula (a), (b) and (c), in addition to other amino acids, are included within the peptides which comprise the invention.

The preferred minimum values for n, m and p have been determined experimentally on the basis of the observation that when the peptide is linear, it should have at least 7 amino acid units and when said peptide is cyclic or a polymer having several cycles, i.e. 2 to 6 cycles, it will have a ring structure that has a minimum of 6 amino acid units; said peptides having a ratio of aliphatic cationic amino acids to hydrophobic amino acids which is equal to or greater than 0.5.

When the peptides are of the formula $(A)_n$, $(AB)_m$ or $(ABC)_p$, i.e. when these formulas do not represent units of a larger peptides, n will be from 7 to 500 and preferably from 7 to 16; m will be from 3 to 200 and preferably from 4 to 20 and p will be from 2 to 100 and preferably from 4 to 20.

Examples of the peptides are listed below.

```
(Lys)10                                             (SEQ ID NO: 1);

(Lys)30                                             (SEQ ID NO: 2);

(Lys)434                                            (SEQ ID NO: 3);

(Lys-Asp)5                                          (SEQ ID NO: 4);

(Lys-Phe)5                                          (SEQ ID NO: 5);

Lys-Phe-Leu-Lys-Lys-Thr-Leu                         (SEQ ID NO: 6);

(Lys-Phe-Leu)2-Lys                                  (SEQ ID NO: 7);

(Lys-Phe-Leu)3-Lys                                  (SEQ ID NO: 8);

(Arg-Tyr-Val)3                                      (SEQ ID NO: 9);

(Lys-Phe-Phe)3-Lys                                  (Seq ID NO: 10);

(Lys-Leu-Leu)3                                      (SEQ ID NO: 11);

(Lys)6(Phe-Lys)2                                    (SEQ ID NO: 12);

Cys-(Lys)5-Cys                                      (SEQ ID NO: 13);
s-----------s

Cys-Lys-Phe-Lys-Lys-Cys                             (SEQ ID NO: 14);
s----------------s

Lys-Phe-Lys-Cys-Lys-Phe-Lys-Phe-Lys-Cys             (SEQ ID NO: 15);
              s-----------------------s

Lys-Leu-Lys-Cys-Lys-Leu-Lys-Leu-Lys-Cys             (SEQ ID NO: 16);
              s-----------------------s

Arg-Thr-Arg-Cys-Arg-Phe-Lys-Arg-Arg-Cys             (SEQ ID NO: 17);
              s-----------------------s

Lys-Cys-(Lys-Phe-Lys)2-Cys-Lys                      (SEQ ID NO: 18);
      s-------------------s

Cys-(Lys)4-(Phe)4-Cys                               (SEQ ID NO: 19);
s-------------------s

Cys-(Lys-Phe-Leu)3-Lys-Cys                          (SEQ ID NO: 20);
s----------------------s

Val-Lys-Ala-Leu-Arg-Val-Arg-Arg-Leu                 (SEQ ID NO: 21);

Lys-Ser-Leu-Ser-Leu-Lys-Arg-Leu-Thr-Tyr-Arg         (SEQ ID NO: 22);

Lys-Val-Arg-Lys-Ser-Phe-Phe-Lys-Val                 (SEQ ID NO: 23);

Phe-Leu-Lys-Pro-Gly-Lys-Val-Lys-Val                 (SEQ ID NO: 24);

Lys-Glu-Leu-Lys-Arg-Ile-Lys-Ile                     (SEQ ID NO: 25);

Lys-Trp-Lys-Ala-Gln-Lys-Arg-Phe-Leu                 (SEQ ID NO: 26);

Lys-Trp-Lys-Ala-Gln-Lys-Arg-Phe-Leu-Lys             (SEQ ID NO: 27);

Lys-Arg-Leu-Lys-Trp-Lys-Tyr-Lys-Gly-Lys-Phe         (SEQ ID NO: 28); and

Cys-Gln-Ser-Trp-Lys-Ser-Ser-Glu-Ile-Arg-Cys-Gly-Lys (SEQ ID NO: 29).
s---------------------------------------s

Cys-Lys-Phe-Leu-Lys-Lys-Cys                         (SEQ ID NO: 30)
```

-continued

```
        s - - - - - - - - - - - s
Lys-Thr-Lys-Cys-Lys-Phe-Leu-Lys-Lys-Cys                (SEQ ID NO: 31)
              s - - - - - - - - - - - s

Lys-Phe-Leu-Lys-Lys-Thr                                (SEQ ID NO: 32)

Cys-Lys-Lys-Leu-Phe-Lys-Cys-Lys-Thr-Lys                (SEQ ID NO: 33)
s - - - - - - - - - - - s

Cys-Lys-Lys-Leu-Phe-Lys-Cys-Lys-Thr                    (SEQ ID NO: 34)
s - - - - - - - - - - - -s

Ile-Lys-Thr-Lys-Cys-Lys-Phe-Leu-Lys-Lys-Cys            (SEQ ID NO: 35)
              s - - - - - - - - - - - s

Ile-Lys-Thr-Lys-Lys-Phe-Leu-Lys-Lys-Thr                (SEQ ID NO: 36)

Ile-Lys-Phe-Leu-Lys-Phe-Leu-Lys-Phe-Leu-Lys            (SEQ ID NO: 37)

Lys-Phe-Leu-Lys-Phe-Leu-Lys                            (SEQ ID NO: 38)

Arg-Tyr-Val-Arg-Tyr-Val-Arg-Tyr-Val                    (SEQ ID NO: 39)

Lys-Phe-Phe-Lys-Phe-Phe-Lys-Phe-Phe                    (SEQ ID NO: 40)

Ile-Lys-Phe-Leu-Lys-Phe-Leu-Lys-Phe-Leu                (SEQ ID NO: 41)

(Lys)⁶Phe-Leu-Phe-Leu                                  (SEQ ID NO: 42)

Cys-Lys-Phe-Lys-Phe-Lys-Phe-Lys-Phe-Cys                (SEQ ID NO: 43)
s----------------------------------s

Lys-Trp-Lys-Ala-Gln-Lys-Arg-Phe-Leu-Lys                (SEQ ID NO: 44)

Lys-Arg-Leu-Lys-Trp-Lys-Tyr-Lys-Gly-Lys-Phe            (SEQ ID NO: 45)
```

The peptides for use in the present invention may be synthesized by classical methods of peptide chemistry using manual or automated techniques as well as by DNA recombinant technology. The synthetic procedure comprises solid phase synthesis by Fmoc chemistry, cleavage (TFA 95%+ Et-(SH)$_2$ 5%) followed by vacuum evaporation. Thereafter, the product is dissolved in 10% acetic acid, extracted with ether, concentrated at 0.1 mg/ml at pH of 6.0–7.5. Stirring under filtered air followed for 1 to 6 hours in case of the Cysteine-containing peptides and finally desalting by reverse phase chromatography is carried out.

A particular automated method of preparing peptides for use in the present invention is based on the use of an automatic synthesizer (Milligen Mod.9050 (MILLIPORE, Burlington, Mass.) on a solid phase support of polyamide/Kieselguhr resin (2.0 g). The amino acids used in the synthesis of the peptide analogs are Fmoc-aa-Opfp derivatives (9-Fluorenylmethylcarbonyl-aa-O-pentafluorophenyl ester) of each amino acid(aa) involved in the considered sequences using 0.8 mol of each amino acid to sequentially form the peptide.

Each cycle of synthesis may be performed at room temperature (20° C.) and involves the following steps of reaction:

Step 1—Deprotection

The first aa Fmoc-protected at the amino group, was treated with a 20% solution of piperidine for 7 minutes in order to remove the Fmoc alpha-protecting group. Washing with dimethylformamide followed for 12 minutes to remove all traces of piperidine. Deprotection and washing were run continuously through the column containing the resin by means of a pump at a flow of 5 ml/min.

Step 2—Activation of the Fmoc-aa-Opfp derivative

The amino and carboxy-protected amino acid due, according to the desired sequence, was activated after its dissolution in 5 ml of dimethylformamide, by a catalytic amount of hydroxybenzotriazol (0.5 ml of a 5% w/v solution in dimethylformamide).

Step 3—Acylation

The activated and protected Fmoc-aa-Opfp derivative was then recycled for 30 minutes through the column by the pump at 5ml/min in order to obtain coupling of the introduced aa at the alpha-amino group (previously deprotected as reported in Step 1) of the amino acid preceding the new one in the desired sequence.

Step 4—Washing

Washing of the matrix in the column followed by dimethylformamide for 2 minutes at 5 ml/min before a new cycle began.

At the completion of the synthesis, the peptide on the resin support was cleaved by 95% Trifluoroacetic acid (TFA) with 5% ethane dithiol as a scavenger, if Cysteine residues were present in the aa sequence, at room temperature for 2 hours. After separation of the cleaved peptide from the resin by filtration, the solution was concentrated by vacuum evaporation to dryness. The collected solid residue was then solubilized in 10% acetic acid at a concentration of 10–20 mg/ml and several extractions by diethyl ether followed (six to eight extractions with half the volume of the peptide solution) in order to remove the scavenger Ethane dithiol. The peptide solution was then neutralized by 0.1 N ammonium hydroxide and adjusted to the concentration of roughly 0.1 mg/ml. The solution was then stirred under air for 1 to 6 hours in order to obtain the selective oxidation of the two sulfhydryl groups belonging to the Cys residues of the sequence. In this way, only monomeric oxidized peptides were obtained with no traces of polymeric material. The solution of oxidized peptide was then desalted by reverse-phase chromatography on SEP-PAK C-18 cartridges (MILLIPORE) and finally freeze dried. The products were analyzed by high-performance liquid chromatography (HPLC) analysis as well as by chemical analysis of the synthetic structures.

Fast atom bombardment may be used to confirm the calculated mass of the peptides.

The vaccines may be administered parenterally, preferably subcutaneously using well known pharmaceutical carriers or inert diluents such as water for injection, sterile normal saline and the like.

The LPS and the peptide may be reacted by combining sterile aqueous solutions of the LPS and the peptide followed by incubation for 15 min. to six hours at temperature from 25° C. to 40° C. Generally, the effective amount of the endotoxoid complex is from 0.1 μg to 50 μg/kg of body weight for a mammal. The endotoxoid complex may be employed in humans and in veterinary practice to prevent sepsis and the toxic effects of endotoxin related shock caused by bacterial infections wherein the causative organism elaborates endotoxin. The endotoxoid complex may be administered prophylactically as a vaccine by giving one or more doses to a subject until a protective level of antibodies is detected by the following test: Enzyme Linked Immunoassay (ELISA) or any other clinically acceptable immunoassay.

Generally, a vaccination regimen may comprise an initial dose of the vaccine followed by from one to four booster inoculations given at intervals of two to four weeks.

The particular dose of a particular endotoxoid complex may be varied within or without the range that is specified herein depending on the particular host. Those who are skilled in the art may ascertain the proper dose using standard procedures. The vaccine of the invention may be monovalent in that it contains one endotoxoid complex derived from the LPS obtained from one species of bacteria or it may be polyvalent and contain a plurality of endotoxoid complexes made from LPS which is obtained different species of bacteria. The endotoxoid complex may also be administered as a part of a multicomponent vaccine such as diphtheria-pertussis-tetanus (DPT) (Tri-immunol, Lederle Laboratories) or diphtheria-pertussis-tetanus-haemophilius) (Tetraimmune, Lederle Laboratories). In such cases, an effective amount of the endotoxoid complex or complexes may be combined with the multicomponent vaccine in order to simultaneously induce multiple antibodies in a host.

The invention also includes the combined administration of the vaccine of the invention with an effective amount of an antibiotic and/ or a peptide as described above to simultaneously treat a gram-negative infection and provide an immunizing dose of the vaccine. The amounts of the peptide to be administered are described in U.S. 5,589,459 and the combined antibiotic-peptide therapy is described in Serial No 08/456,112, both of which are incorporated by reference.

DESCRIPTION OF THE PREFERRED EMBODIMENTS

EXAMPLE

Preparation of Antigens

LPS from *N. meningitidis* A1, BB431, 44/77 and purified *N. meningitidis* LPS A1 were prepared and characterized according to the method of Gu and Tsai, Infect. Immun. (1993); 61:1873–1879, which is incorporated by reference. The cyclic peptide, described herein by as SAEP2 was synthesized on solid phase, oxidized and characterized according to the methods set forth in Science (1993): 259:361–365, which is incorporated by reference.

The covalent conjugate BSA-LPS A1 was prepared as follows: LPS A1 (5 mg/ml) in PBS., containing two reactive moles of amino group per mole of oligosaccharide-lipid A monomer, was transformed to the mono-succinimidyl ester by incubation (60 min at room temperature) with the bis-succinimidyl ester of adipic acid (0.7 mg/ml) in dimethyl-sulfoxide (DMSO), according to the procedure reported for amino-activated bacterial capsular oligosaccharides in Mol Immunol (1985):22:907–919.

The LPS A1 derivative had more than 98% of the amino groups contained in its structure transformed into highly reactive ester groups as determined by the trinitrobenzene sulfonic acid (TNBS) reaction. The ester-derivative of LPS A1 was then mixed with a sodium bicarbonate solution pH=8.0 containing 0.9 mg/ml of BSA. The stoichiometry of the reagents is equivalent to a molar ratio between the amino groups of BSA:monoester groups of LPS A1=2. The solution was stirred for 4 hours at room temperature and the BSA-LPS A1 conjugate was recovered by precipitation with ethanol (60% v/v final concentration), solubilized in 0.1 M sodium bicarbonate and finally purified using gel chromatography (Sepharose, Pharmacia) sterile filtered using a 0.22 μm membrane and freeze dried. The conjugate is consistent with a ratio of BSA:LPS A1=1(w/w).

Preparation of Vaccines

Complexes of the SAEP2 peptide with both LPS A1 and BSA-LPS A1 conjugate were prepared by combining sterile solutions of LPS A1 or BSA:LPS A1 with a 0.1 to 5% (w/w) solution of SAEP2 peptide at a ratio of LPS/SAEP2 peptide of 1:250(w/w). The solutions were incubated for 30 min. at 37° C. Sodium merthiolate 0.01% (w/v) was added as a preservative and the products were stored at 4° C. The immunizing dose of LPS A1 was in the range of 0.5–5 μg in 0.2 ml, in the formulations of vaccine tested.

Testing

Figure 1:
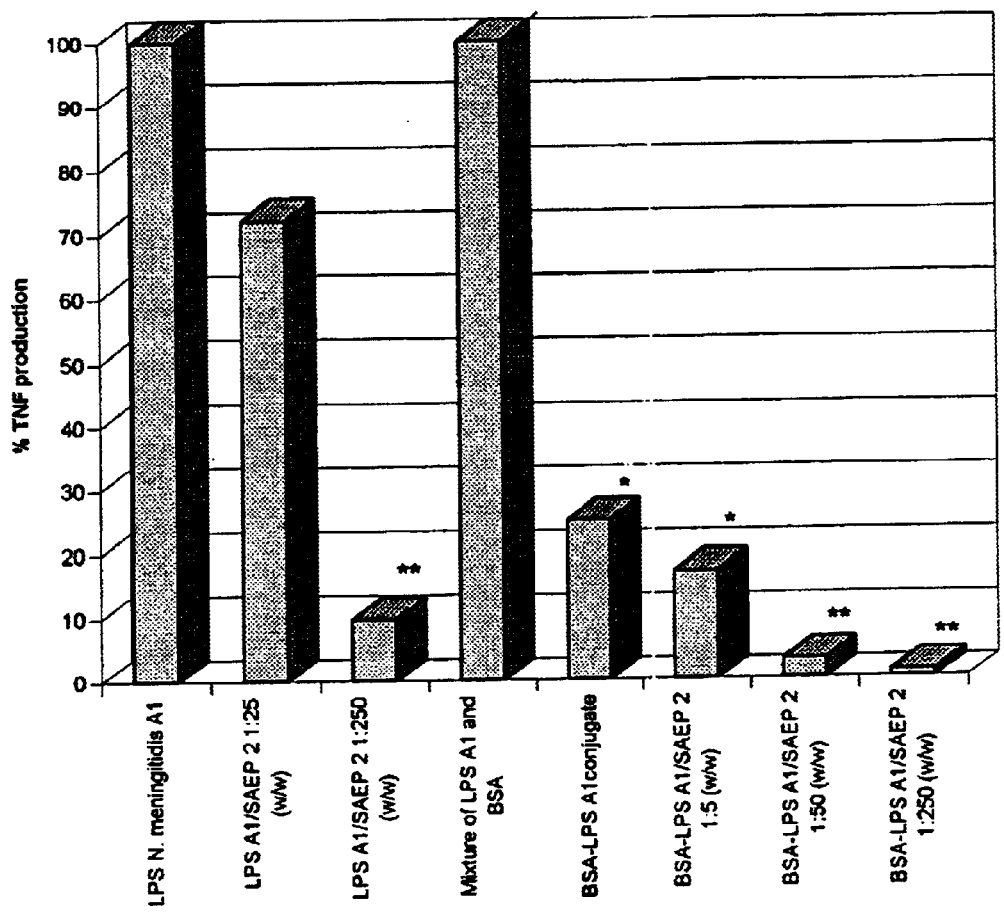
FIG. 1 is graph which compares the percent of TNF produced "in vivo" by LPS A1 and various LPS A1 conjugate antigens detoxified by a peptide which is representative of the class of peptides which may be used in the present invention.

The safety of the LPS A1/SAEP2 peptide complex was confirmed "in vitro" by the lack of pyrogenic activity tested by Lipid A-induced LAL clotting and "in vivo" by the determination of TNF (the mediator of toxicity) titers induced by the vaccines in mice (strains SW and CD1). TNF was inhibited by 90% when the LPS A1/SAEP2 peptide complex (1:250 w/w ratio) was employed and TNF was inhibited by 98% when the conjugate BSA-LPS A1/SAEP2 peptide complex (1:250 w/w ratio) was employed. The results for the various TNF determinations are shown in FIG. 1.

The immunogenicity of the LPS A1/SAEP2 peptide complex was determined by comparing the kinetic pattern of the IgG antibodies specific for LPS A1 which are induced by LPS A1; LPS A1/SAEP2 peptide complex; and BSA-LPS A1; and BSA-LPS A1/SAEP2 peptide complex. The results are shown in FIG. 2a and FIG. 2b. The test data show that immunogenicity of endotoxin A1 (LPS A1/SAEP2 peptide complex) is comparable to that induced by the conjugates BSA-LPS A1 peptide complex. Therefore, toxicity and immunogenicity have been dissociated in an endotoxoid.

EXAMPLE 2

LPS from *N. meningitidis* group A (LPS A1) and *Salmonella enterica* (serotype *typhimurium*, LPS Ty) were used to prepare vaccines from two groups of structurally different LPS (R- and S-like chemotype) that originated from clinical isolates of extracellular and intracellular Gram-negative bacteria, respectively. Both LPS' exhibit an active lipid A moiety with a binding site which is stoichiometrically saturated "in vitro", with high affinity, by a synthetic cyclic peptide (SAEP2) which exemplifies the peptides of the invention ) For "in vivo" testing, peptide complexes were prepared at a ratio of (a) 1:250; 1:1000 and 1:2500 of LPS A1:peptide and LPS Ty:peptide.

The two endotoxoids (A1 and Ty) were completely nontoxic with respect to LPS, as demonstrated by the level of TNF systemically released in mice after four injections of the antigens (FIG. 3). Comparable results were obtained in rabbits by using a hemorrhagic necrosis test or Schwartzman reaction.

Outbred mice were immunized subcutaneously, three weeks apart, by plain LPS A1 and LPS Ty in parallel with the homologous endotoxoids prepared by complex formation with a cyclic peptide (SAEP2 was used as an example). Serum immune response was assayed for specific anti-LPS IgG isotype antibodies, two weeks following each administration. LPS A1 and LPS Ty have shown a minimum immunogenic activity at the dose of 5 ug/mouse. The homologous endotoxoids have expressed, at a dose ten times lower (0.5 µg), an immunogenic activity comparable to that obtained with a dose of 5 µg of plain LPS.

To explain this observation, it is hypothesized that there is a downregulating activity of TNF on T-cells. For this purpose, mice were immunized with plain LPS A1, whose toxicity was abrogated by the previous administration of a characterized anti-TNF monoclonal antibody. Although the toxicity of plain LPS A1 was abrogated by the anti-TNF treatment (FIG. 3), no significant increase in the immunogenicity of LPS was detected, in contrast to the homologous endotoxoid (FIG. 4a), suggesting that while TNF is the recognized mediator of LPS toxicity, it is not significantly involved in the immunogenic activity of LPS.

The endotoxoid-induced IgG antibodies were specific for the core oligosaccharide chain of LPS A1 and for the O-saccharide chain of LPS Ty respectively (FIG. 5a and FIG. 5b). The endotoxoids were functional in fixing and activating homologous and heterologous species of complement and were completely protective in a significant model of salmonella infection (FIG. 6a and FIG. 6b). Furthermore, the endotoxoid-induced IgG antibodies were able to passively protect the animals from the endotoxemic effects, detectable by serum TNF release, of a systemic challenge by homologous LPS (Table I).

Table I

Effect of anti LPS A1 polyclonal IgG antibodies on the inhibition of serum TNF production in CD! mice challenged i.v. with homologous *N. meningitidis* A1 LPS and heterologous *E. coli* 055 B5 LPS. Data represent mean of two independent experiments with 5 mice/group. IgG anti LPS A1 were injected i.v. 30 minutes before either *N. meningitidis* A1 LPS or *E. coli* 055:B5 LPS i.v. challenge.

TABLE I

Effect of anti LPS A1 polyclonal IgG antibodies on the inhibition of serum TNF production in CD! mice challenged i.v. with homologous *N. meningitidis* A1 LPS and heterologous *E. coli* 055 B5 LPS. Data represent mean of two independent experiments with 5 mice/group. IgG anti LPS A1 were injected i.v. 30 minutes before either *N. meningitidis* A1 LPS or *E. coli* 055:B5 LPS i.v. challenge.

| Mice | IgG antiLPS A1 | CHALLENGE | |
|---|---|---|---|
| | | LPS A1 | LPS B5 |
| 10 | saline | 6,110+/−2,062 | 2,371+/−1,471 |
| 10 | 0.25 | 1,579+/−591 (inhibition 74%, $p < 0.01$) | 2,068+/−1,864 |

These experimental results show the protective activity, in a mammalian host, of a bacterial endotoxoid originating from LPS of either extracellular or intracellular gram-negative pathogens.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A vaccine for preventing gram-negative infections which comprises a complex obtained by combining LPS free or in conjugate form with a stoichiometric excess of a peptide, on a weight basis relative to said LPS, said peptide selected from the group consisting of:
   (a) $(A)_n$ wherein A is Lysine or Arginine and n is an integer with a minimum value of 7; (b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

2. A vaccine as defined in claim 1 wherein the peptide is a linear or cyclic peptide comprising units of formula selected from the group consisting of:
   (a) $(A)_n$ wherein A is Lysine or Arginine and n is an integer with a value of 7 to 16; (b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a value of 4 to 20; and (c) $(ABC)_p$ wherein A is a caticinic amino acid which is Lysine or Arginme; B and C are hydrophobic amino acids which may be the same or different and are selected from the group consisting of Valine, Leucine, Isoleucine, Tyrosine, Phenylalanine and Tryptophan; p is an integer with a value of 4 to 20.

3. A vaccine as defined in claim 1 wherein the LPS is derived from *N. meningitidis*.

4. A vaccine as defined in claim 1 wherein the LPS is derived from *Salmonella typhi*.

5. A vaccine as defined in claim 1 where the amount of peptide is from 2–10 to 2–5000 times the weight of the LPS.

6. A vaccine as defined in claim 1 wherein the peptide has units comprising $(AB)_m$.

7. A vaccine as defined in claim 1 wherein the peptide has units comprising $(ABC)_p$.

8. A vaccine as defined in claim 1 wherein the peptide comprises: $(Lys)_{10}$ (SEQ ID NO: 1).

9. A vaccine for preventing gram-negative infections which comprises a complex obtained by combining LPS free or in conjugate form with a stoichiometric excess of a peptide, on a weight basis relative to said LPS wherein the peptide comprises:
   $(Lys-Phe)_5$ (SEQ ID NO: 5).

10. A vaccine for preventing gram-negative infections which comprises a complex obtained by combining LPS free or in conjugate form with a stoichiometric excess of a peptide on a weight basis relative to said LPS wherein the peptide comprises:
    Lys-Phe-Leu-Lys-Lys-Thr-Leu (SEQ ID NO: 6).

11. A vaccine for preventing gram-negative infections which comprises a complex obtained by combining LPS free or in conjugate form with a stoichiometric excess of a peptide on a weight basis relative to said LPS wherein the peptide comprises:
    $(Lys-Phe-Leu)_2$-Lys (SEQ ID NO: 7).

12. A vaccine for preventing gram-negative infections which comprises a complex obtained by combining LPS free or in conjugate form with a stoichiometric excess of a peptide on a weight basis relative to said LPS wherein the peptide comprises:
    $(Lys-Phe-Leu)_3$-Lys (SEQ ID NO: 8).

13. A vaccine for preventing gram-negative infections which comprises a complex obtained by combining LPS free or in conjugate form with a stoichiometric excess of a peptide on a weight basis relative to said LPS wherein the peptide comprises:
    $(Arg-Tyr-Val)_3$ (SEQ ID NO: 9).

14. A vaccine for preventing gram-negative infections which comprises a complex obtained by combining LPS free or in conjugate form with a stoichiometric excess of a peptide on a weight basis relative to said LPS wherein the peptide comprises:
    $(Lys-Phe-Phe)_3$-Lys (SEQ ID NO: 10).

15. A vaccine for preventing gram-negative infections which comprises a complex obtained by combining LPS free or in conjugate form with a stoichiometric excess of a peptide on a weight basis relative to said LPS wherein the peptide comprises:
    $(Lys-Leu-Leu)_3$ (SEQ ID NO: 11).

16. A vaccine for preventing gram-negative infections which comprises a complex obtained by combining LPS free or in conjugate form with a stoichiometric excess of a peptide on a weight basis relative to said LPS wherein the peptide comprises:
    $(Lys)_6(Phe-Lys)_2$ (SEQ ID NO: 12).

17. A vaccine for preventing gram-negative infections which comprises a complex obtained by combining LPS free or in conjugate form with a stoichiometric excess of a peptide on a weight basis relative to said LPS wherein the peptide comprises:

```
Cys-Lys-Phe-Lys-Lys-Cys      (SEQ ID NO: 14)
 s-------------------s.
```

18. A vaccine for preventing gram-negative infections which comprises a complex obtained by combining LPS free or in conjugate form with a stoichiometric excess of a peptide on a weight basis relative to said LPS wherein the peptide comprises:

```
Lys-Phe-Lys-Cys-Lys-Phe-Lys-Phe-Lys-Cys    (SEQ ID NO: 15)
         s----------------------s.
```

19. A vaccine for preventing gram-negative infections which comprises a complex obtained by combining LPS free or in conjugate form with a stoichiometric excess of a peptide on a weight basis relative to said LPS wherein the peptide comprises:

```
Lys-Leu-Lys-Cys-Lys-Leu-Lys-Leu-Lys-Cys     (SEQ ID NO: 16)
          s-----------------------s.
```

20. A vaccine for preventing gram-negative infections which comprises a complex obtained by combining LPS free or in conjugate form with a stoichiometric excess of a peptide on a weight basis relative to said LPS wherein the peptide comprises:

```
Arg-Thr-Arg-Cys-Arg-Phe-Lys-Arg-Arg-Cys     (SEQ ID NO: 17)
          s-----------------------s.
```

21. A vaccine for preventing gram-negative infections which comprises a complex obtained by combining LPS free or in conjugate form with a stoichiometric excess of a peptide on a weight basis relative to said LPS wherein the peptide comprises:

```
Lys-Cys-(Lys-Phe-Lys)₂-Cys-Lys     (SEQ ID NO: 18)
       s------------------s.
```

22. A vaccine for preventing gram-negative infections which comprises a complex obtained by combining LPS free or in conjugate form with a stoichiometric excess of a peptide on a weight basis relative to said LPS wherein the peptide comprises:

```
       Cys-(Lys)₄-(Phe)₄-Cys     (SEQ ID NO: 19)
       s------------------s.
```

23. A vaccine for preventing gram-negative infections which comprises a complex obtained by combining LPS free or in conjugate form with a stoichiometric excess of a peptide on a weight basis relative to said LPS wherein the peptide comprises:

```
    Cys-(Lys-Phe-Leu)₃-Lys-Cys    (SEQ ID NO: 20)
    s----------------------s.
```

24. A vaccine for preventing gram-negative infections which comprises a complex obtained by combining LPS free or in conjugate form with a stoichiometric excess of a peptide on a weight basis relative to said LPS wherein the peptide comprises:
   Val-Lys-Ala-Leu-Arg-Val-Arg-Arg-Leu (SEQ ID NO: 21).

25. A vaccine for preventing gram-negative infections which comprises a complex obtained by combining LPS free or in conjugate form with a stoichiometric excess of a peptide on a weight basis relative to said LPS wherein the peptide comprises:
   Lys-Ser-Leu-Ser-Leu-Lys-Arg-Leu-Thr-Tyr-Arg (SEQ ID NO: 22).

26. A vaccine for preventing gram-negative infections which comprises a complex obtained by combining LPS free or in conjugate form with a stoichiometric excess of a peptide on a weight basis relative to said LPS wherein the peptide comprises:
   Lys-Val-Arg-Lys-Ser-Phe-Phe-Lys-Val (SEQ ID NO: 23).

27. A vaccine for preventing gram-negative infections which comprises a complex obtained by combining LPS free or in conjugate form with a stoichiometric excess of a peptide on a weight basis relative to said LPS wherein the peptide comprises:
   Phe-Leu-Lys-Pro-Gly-Lys-Val-Lys-Val (SEQ iD NO: 24).

28. A vaccine for preventing gram-negative infections which comprises a complex obtained by combining LPS free or in conjugate form with a stoichiometric excess of a peptide on a weight basis relative to said LPS wherein the peptide is of the formula:
   Lys-Glu-Leu-Lys-Arg-Ile-Lys-Ile (SEQ ID NO: 25).

29. A vaccine for preventing gram-negative infections which comprises a complex obtained by combining LPS free or in conjugate form with a stoichiometric excess of a peptide on a weight basis relative to said LPS wherein the peptide is of the formula:
   Lys-Trp-Lys-Ala-Gln-Lys-Arg-Phe-Leu (SEQ ID NO: 26).

30. A vaccine for preventing gram-negative infections which comprises a complex obtained by combining LPS free or in conjugate form with a stoichiometric excess of a peptide on a weight basis relative to said LPS wherein the peptide is of the formula:
   Lys-Trp-Lys-Ala-Gln-Lys-Arg-Phe-Leu-Lys (SEQ ID NO: 27).

31. A vaccine for preventing gram-negative infections which comprises a complex obtained by combining LPS free or in conjugate form with a stoichiometric excess of a peptide on a weight basis relative to said LPS wherein the peptide is of the formula:
   Lys-Arg-Leu-Lys-Trp-Lys-Tyr-Lys-Gly-Lys-Phe (SEQ ID NO: 28).

32. A vaccine for preventing gram-negative infections which comprises a complex obtained by combining LPS free or in conjugate form with a stoichiometric excess of a peptide on a weight basis relative to said LPS wherein the peptide is of the formula:

```
Lys-Thr-Lys-Cys-Lys-Phe-Leu-Lys-Lys-Cys    (SEQ ID NO: 31)
        s - - - - - - - - - - - s.
```

33. A vaccine for preventing gram-negative infections which comprises a complex obtained by combining LPS free or in conjugate form with a stoichiometric excess of a peptide on a weight basis relative to said LPS wherein the peptide is of the formula:

```
    Cys-Lys-Phe-Leu-Lys-Lys-Cys    (Seq ID NO: 30)
    s-----------------------s.
```

34. A vaccine for preventing gram-negative infections which comprises a complex obtained by combining LPS free or in conjugate form with a stoichiometric excess of a peptide on a weight basis relative to said LPS wherein the peptide is of the formula:
Lys-Phe-Leu-Lys-Lys-Thr (SEQ ID NO: 32).

35. A vaccine for preventing gram-negative infections which comprises a complex obtained by combining LPS free or in conjugate form with a stoichiometric excess of a peptide on a weight basis relative to said LPS wherein the peptide is of the formula:

```
Cys-Lys-Lys-Leu-Phe-Lys-Cys-Lys-Thr-Lys    (SEQ ID NO: 33)
 s - - - - - - - - - - - s.
```

36. A vaccine for preventing gram-negative infections which comprises a complex obtained by combining LPS free or in conjugate form with a stoichiometric excess of a peptide on a weight basis relative to said LPS wherein the peptide is of the formula:

```
Cys-Lys-Lys-Leu-Phe-Lys-Cys-Lys-Thr    (SEQ ID NO: 34)
 s - - - - - - - - - - - s.
```

37. A vaccine for preventing gram-negative infections which comprises a complex obtained by combining LPS free or in conjugate form with a stoichiometric excess of a peptide on a weight basis relative to said LPS wherein the peptide is of the formula:

```
Ile-Lys-Thr-Lys-Cys-Lys-Phe-Leu-Lys-Lys-Cys   (SEQ ID NO: 35)
            s - - - - - - - - - - - s.
```

38. A vaccine for preventing gram-negative infections which comprises a complex obtained by combining LPS free or in conjugate form with a stoichiometric excess of a peptide on a weight basis relative to said LPS wherein the peptide is of the formula:
Ile-Lys-Thr-Lys-Lys-Phe-Leu-Lys-Lys-Thr (SEQ ID NO: 36).

39. A vaccine for preventing gram-negative infections which comprises a complex obtained by combining LPS free or in conjugate form with a stoichiometric excess of a peptide on a weight basis relative to said LPS wherein the peptide comprises:
Ile-Lys-Phe-Leu-Lys-Phe-Leu-Lys-Phe-Leu-Lys (SEQ ID NO: 37).

40. A vaccine for preventing gram-negative infections which comprises a complex obtained by combining LPS free or in conjugate form with a stoichiometric excess of a peptide on a weight basis relative to said LPS wherein the peptide comprises:
Lys-Phe-Leu-Lys-Phe-Leu-Lys (SEQ ID NO: 38).

41. A vaccine for preventing gram-negative infections which comprises a complex obtained by combining LPS free or in conjugate form with a stoichiometric excess of a peptide on a weight basis relative to said LPS wherein the peptide comprises:
Arg-Tyr-Val-Arg-Tyr-Val-Arg-Tyr-Val (SEQ ID NO: 39).

42. A vaccine for preventing gram-negative infections which comprises a complex obtained by combining LPS free or in conjugate form with a stoichiometric excess of a peptide on a weight basis relative to said LPS wherein the peptide comprises:
Lys-Phe-Phe-Lys-Phe-Phe-Lys-Phe-Cys (SEQ ID NO: 40).

43. A vaccine for preventing gram-negative infections which comprises a complex obtained by combining LPS free or in conjugate form with a stoichiornetric excess of a peptide on a weight basis relative to said LPS wherein the peptide comprises:
Ile-Lys-Phe-Leu-Lys-Phe-Leu-Lys-Phe-Leu (SEQ ID NO: 41).

44. A vaccine for preventing gram-negative infections which comprises complex obtained by combining LPS free or in conjugate form with a stoichiometric excess of a peptide on a weight basis relative to said LPS wherein the peptide is of the formula:

(Lys)₆Phe-Leu-Phe-Leu (SEQ ID NO: 42).

45. A vaccine as defined in claim 1 wherein the peptide comprises:

```
Cys-Lys-Phe-Lys-Phe-Lys-Phe-Lys-Phe-Cys    (SEQ ID NO: 43)
s-----------------------------------s.
```

46. A vaccine for preventing gram-negative infections which comprises complex obtained by combining LPS free or in conjugate form with a stoichiometric excess of peptide on a weight basis relative to said LPS wherein the peptide is of the formula:

Lys-Trp-Lys-Ala-Gln-Lys-Arg-Phe-Leu-Lys (SEQ ID NO: 44).

47. A vaccine as defined in claim 1 wherein the peptide comprises:

Lys-Arg-Leu-Lys-Trp-Lys-Tyr-Lys-Gly-Lys-Phe (SEQ ID NO: 45).

48. A method for the preparation of a vaccine for prevention of gram-negative infections, said method comprising combining LPS with a stoichiometric excess of a peptide on a weight basis relative to said LPS, said peptide selected from the group consisting of:

(a) $(A)_n$ wherein A is Lysine or Arginine and n is an integer with a minimum value of 7; (b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

49. A vaccine as defined in claim 1 which is combined or administered with other vaccine components.

50. A vaccine as defined in claim 1 which contains an LPS peptide complex derived from more than one species of bacteria.

51. A vaccine for prevention of gram-negative infections which comprises a complex obtained by combining LPS free or in conjugate form with a stoichiometric excess of a peptide:LPS where there is an excess of from 2 to 5000 times by weight of peptide, said peptide being selected from the group consisting of:

(a) $(A)_n$ wherein A is Lysine or Arginine and n is an integer with a minimum value of 7; (b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer-with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

52. A vaccine for preventing gram-negative infections which comprises a complex obtained by combining LPS in a free form or in conjugate form with a stoichiometric excess of a peptide on a weight basis relative to said LPS of the formula:

```
Cys-(Lys)₅-Cys         (SEQ ID NO: 13)
s-----------s.
```

53. A vaccine as defined in claim 1 wherein the LPS is derived from non-typable *H. influenzae*.

54. A vaccine as defined in claim 1 wherein the LPS is derived from *N. meningitidis, H. influenzae, Moraxella catharralis, Pseudomonas aeruginosa, Salmonella enterica* and *Escherichia coli*.

55. A vaccine as defined in claim 54 wherein the LPS is derived from *Salmonella enterica*.

56. A vaccine as defined in claim 54 wherein the LPS is derived from *H. influenzae*.

57. A vaccine as defined in claim 54 wherein the LPS is derived from *N. meningitidis*.

58. A vaccine as defined in claim 54 wherein the LPS is derived from *Moraxella catharralis*.

59. A vaccine as defined in claim 54 wherein the LPS is derived from *Escherichia coli*.

60. A vaccine for preventing gram-negative infections which comprises a complex obtained by combining LPS free or in conjugate form with a stoichiometric excess of peptide:LPS where there is an excess of from 2 to 2500 times by weight of peptide, said peptide consisting essentially of a peptide selected from the group consisting of:

(a) $(A)_n$ wherein A is Lysine or Arginine and n is an integer with a minimum value of 7; (b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2.

61. A vaccine for preventing gram-negative infections as defined in claim 60 which comprises a complex obtained by combining LPS free or in conjugate form with a stoichiometric excess of peptide:LPS where there is an excess of from 250 to 2500 times by weight of peptide.

* * * * *